United States Patent [19]

Fukuda et al.

[11] Patent Number: 5,675,036

[45] Date of Patent: Oct. 7, 1997

[54] PROCESS FOR PREPARING AROMATIC AMIDE COMPOUND

[75] Inventors: Etsuko Fukuda, Yamatokoriyama; Atsushi Furutani; Hideki Ushio, both of Takatsuki; Hirokazu Murata, Ibaraki, all of Japan

[73] Assignee: Sumitomo Chemical Company, Limited, Osaka, Japan

[21] Appl. No.: 673,441

[22] Filed: Jun. 28, 1996

[30] Foreign Application Priority Data

Jun. 29, 1995 [JP] Japan .................................. 7-163551

[51] Int. Cl.$^6$ ........................................ C07C 231/02

[52] U.S. Cl. ........................................ 564/142

[58] Field of Search ........................................ 564/142

[56] References Cited

FOREIGN PATENT DOCUMENTS

| 0 634 409 A1 | 1/1995 | European Pat. Off. . |
|---|---|---|
| 3-95144 | 4/1991 | Japan . |
| 0395144 | 4/1991 | Japan . |
| 7-330701 | 12/1995 | Japan . |
| 1 482 195 | 8/1977 | United Kingdom . |
| WO 94/12492 | 6/1994 | WIPO . |

OTHER PUBLICATIONS

Patent Abstract of Japan, JP-A-03-095144, Production of Aminophenol Derivative, H. Wakatsuka et al. Apr. 19, 1991.

*Primary Examiner*—Peter O'Sullivan
*Attorney, Agent, or Firm*—Cushman Darby & Cushman IP Group of Pillsbury Madison & Sutro, LLP

[57] ABSTRACT

3-[4-(4-Phenyl-1-butoxy)benzoyl]amino-2-hydroxyacetophenone is prepared by reacting a benzoate ester with a halobutylbenzene in the presence of a basic compound and an aprotic polar compound in an aromatic hydrocarbon solvent to obtain a corresponding ether, alkali hydrolyzing the ether in an aromatic hydrocarbon solvent and precipitating a hydrolysate with an acid to obtain 4-(4-phenyl-1-butoxy)benzoic acid, reacting a halogenating agent with this benzoic acid derivative in an aromatic hydrocarbon solvent to obtain an acid halide, and reacting the acid halide in an aromatic hydrocarbon solvent with a corresponding aromatic amine.

8 Claims, No Drawings

PROCESS FOR PREPARING AROMATIC AMIDE COMPOUND

BACKGROUND OF THE INVENTION

1. Field of the Invention

The present invention relates to an industrially advantageous process for preparing an aromatic amide compound which is useful as an intermediate in the preparation of a medicine.

2. Description of the Related Art

JP-A-3-95144 discloses a process for preparing 2-acetyl-6-[4-(4-phenylbutoxy)benzoyl]aminophenol from a p-hydroxybenzoate ester, a 1-halogeno-4-phenylbutane and an acetylaminophenol. However, a yield of the desired compound in the disclosed working example is not high enough. In addition, a process condition in each step is not necessarily satisfactory as an industrial preparation method. Then, an improvement of such process has been sought.

SUMMARY OF THE INVENTION

An object of the present invention is to provide an industrially advantageous process for preparing a specific aromatic amide compound.

According to the present invention, there is provided a process for preparing a compound of the formula (1):

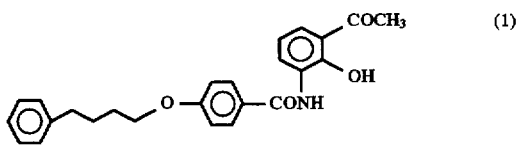

comprising the steps of:

reacting a benzoate of the formula (2):

wherein R is a straight or branched lower alkyl group and a haloalkylbenzene of the formula (3):

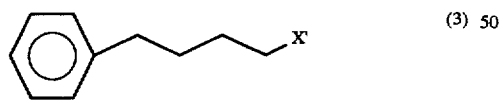

wherein $X^1$ is a halogen atom in the presence of a basic compound and an aprotic polar compound in an aromatic hydrocarbon solvent to obtain an ether of the formula (4):

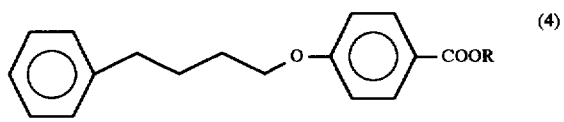

wherein R is the same as defined above, alkali hydrolyzing said ether (4) in an aromatic hydrocarbon solvent and precipitating a hydrolysate with an acid to obtain a benzoic acid derivative of the formula (5):

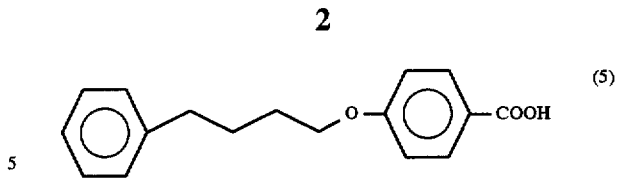

reacting said benzoic acid derivative (5) in an aromatic hydrocarbon solvent with a halogenating agent to obtain an acid halide of the formula (6):

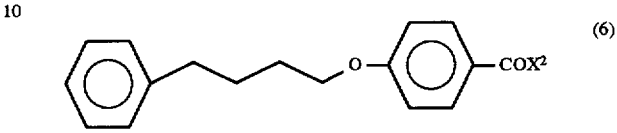

wherein $X^2$ is a halogen atom, and reacting said acid halide (6) in an aromatic hydrocarbon solvent with an aromatic amine of the formula (7):

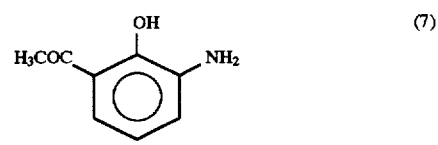

The present invention has been completed based on the finding that, in the preparation of 2-acetyl-6-[4-(4-phenylbutoxy)benzoyl]aminophenol from a p-hydroxybenzoate ester, a 1-halogeno-4-phenylbutane and an acetylaminophenol, when an aromatic hydrocarbon is used as a solvent in all steps of the process, and the specific compounds are present in the step for the preparation of the ether of the formula (4), the desired final compound is obtained in a high yield, and post-treatment after each step is simplified greatly.

The aromatic amide compound prepared by the process of the present invention can be converted to a compound of the formula:

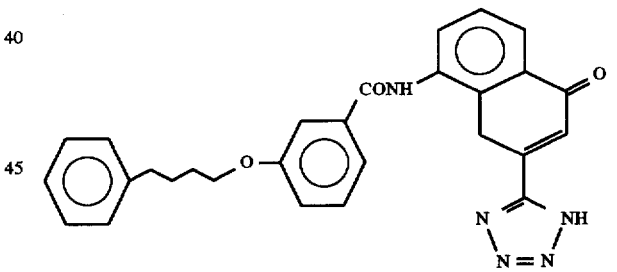

by a known process, for example, the process described in JP-A-3-95144. This compound is useful as an agent for treating various allergic diseases.

DETAILED DESCRIPTION OF THE INVENTION

Hereinafter, the present invention will be explained in detail.

Preparation of the ether (4)

The ether (4) is prepared by reacting the benzoate (2) and the haloalkylbenzene (3) in the presence of the basic compound and the aprotic polar compound in an aromatic hydrocarbon solvent.

The group R in the benzoate (2) and the ether (4) is a straight or branched lower alkyl group having 1 to 8 carbon atoms, such as a methyl group, an ethyl group, a propyl group, a butyl group, a pentyl group, and so on.

Examples of the halogen atom for $X^1$ of the haloalkylbenzene (3) are a chlorine atom, a bromine atom, an iodine atom, and so on.

The aromatic hydrocarbon solvent comprises an aromatic hydrocarbon as a major or a sole component in an amount of not less than 50 weight %, preferably not less than 80 weight %, more preferably not less than 90 weight %.

Preferred examples of the aromatic hydrocarbon solvent are benzene, toluene, xylene, monochlorobenzene, dichlorobenzene, and so on.

The kind of the aromatic hydrocarbon solvent to be used in the steps of the process of the present invention is preferably the same for simple operations.

An amount of the solvent is usually from 1 to 10 times volume, preferably 1 to 5 times volume in relation to the haloalkylbenzene (3).

Examples of the basic compound are hydrides of alkali metals and alkaline earth metals such as sodium hydride, potassium hydride, calcium hydride, etc.; hydroxides of alkali metals and alkaline earth metals such as lithium hydroxide, sodium hydroxide, potassium hydroxide, calcium hydroxide, barium hydroxide, etc.; iron hydroxide; carbonates of alkali metals and alkaline earth metals such as lithium carbonate, sodium carbonate, potassium carbonate, calcium carbonate, barium carbonate, etc.; and hydrogencarbonates of alkali metals such as sodium hydrogencarbonate, potassium hydrogencarbonate, etc.

Among them, the carbonates of the alkali metals and alkaline earth metals are preferred.

An amount of the basic compound is usually from 1 to 5 moles, preferably 1 to 3 moles per one mole of the benzoate (2).

In this step, together with the above basic compound, the aprotic polar compound is used, whereby the reaction rate can be significantly increased.

Examples of the aprotic polar compound are sulfoxides such as dimethylsulfoxide; sulfones such as sulfolane; amides such as N-methyl-2-pyrrolidone; nitriles such as acetonitrile; formamides such as N,N-dimethylformamide; phosphorylamides such as hexamethylphosphoric triamide; ketones such as acetone, methyl ethyl ketone and methyl isobutyl ketone; ethers such as tetrahydrofurane, ethylene glycol dimethyl ether and polyethylene glycol; and so on. Among them, dimethylsulfoxide, sulfolane and N-methyl-2-pyrrolidone are preferred. These compounds may be used independently or in admixture of two or more of them.

An amount of the aprotic polar compound is usually at least 0.1 mole, preferably at least 0.2 mole, more preferably at least 0.4 mole per one mole of the haloalkylbenzene (3) in view of the reaction rate. The amount of the aprotic polar compound does not exceed usually 5 moles, preferably 3 moles, more preferably 2 moles per one mole of the haloalkylbenzene (3) in view of separation of an organic layer and an aqueous layer when washing with water is performed in the post-treatment in this step or in the subsequent reaction steps.

A reaction temperature in the above step is usually from $-50°$ to $+150°$ C., preferably from $-30°$ to $110°$ C. while the upper limit of the reaction temperature may depend on the boiling point of the solvent.

A reaction time is not limited, and a reaction can be terminated when the benzoate (2) or the haloalkylbenzene (3) disappears.

After the completion of the reaction, in general, the reaction mixture is washed with water to remove the basic compound, formed salts and/or the aprotic polar compound, and used in the next reaction step, while the reaction mixture as such may be used in the next reaction step. Usually, the ether (4) is not isolated and is used in the next step in the form of a solution in the aromatic hydrocarbon solvent, while the ether (4) may be isolated and used in the next step.

Preparation of the benzoic acid derivative (5)

The ether (4) in the aromatic hydrocarbon solvent is alkali hydrolyzed and a resultant hydrolysate is precipitated with an acid to obtain the benzoic acid derivative (5).

Examples of the alkali to be used are inorganic bases such as alkali metal hydroxides (e.g. sodium hydroxide, potassium hydroxide, etc.), alkaline earth metal hydroxides (e.g. calcium hydroxide, barium hydroxide, etc.), and the like.

An amount of the alkali is at least one equivalent to the ether (4).

In general, water to be consumed in the hydrolysis is supplied in the form of an aqueous solution of the alkali. An amount of water is usually from 0.2 to 10 wt. parts, preferably 0.5 to 5 wt. parts per one wt. part of the ether (4).

In this step, the addition of an alcohol such as methanol, ethanol, propanol, and so on will accelerate the reaction greatly.

An amount of the alcohol is usually from 0.1 to 5 wt. parts per one wt. part of the ether (4).

A reaction temperature in the above step is usually from $-30°$ to $+200°$ C., preferably from $-20°$ to $150°$ C., while the upper limit of the reaction temperature may depend on the boiling point of the solvent.

A reaction time is not limited, and a reaction can be terminated when the ether (4) disappears.

When the alcohol is used, the hydrolysis can proceed while distilling the alcohol off, or the alcohol can be distilled off after the completion of the hydrolysis. Alternatively, it is possible to use the reaction mixture as such in the next reaction step without removing the alcohol.

A salt of the benzoic acid derivative (5), a hydrolysate, is extracted in an organic layer by acidifying the aqueous layer with an acid such as sulfuric acid, hydrochloric acid, and so on. In general, the organic layer is dehydrated by azeotropic distillation or by the use of a dehydrating agent, and a solution of the benzoic acid derivative (5) in the aromatic hydrocarbon solvent is used in the next reaction step, while the benzoic acid derivative (5) may be isolated and used in the next step.

Preparation of the acid halide (6)

The benzoic acid derivative (5) in the aromatic hydrocarbon solvent is reacted with a halogenating agent to obtain the acid halide (6).

$X^2$ of the acid halide (6) is a halogen atom such as a chlorine atom, a bromine atom, an iodine atom, and so on.

The halogenation reaction of the benzoic acid derivative (5) may be performed by any of conventional halogenation reactions.

Examples of the halogenating agent used in this reaction are thionyl halides and sulfuryl halides (e.g. thionyl chloride, thionyl bromide, sulfuryl chloride, etc.), phosphorus halides (e.g. phosphorus pentachloride, phosphorus trichloride, phosphorus pentabromide, phosphorus tribromide, phosphorus triiodide, etc.), and phosgene compounds (e.g. phosgene, diphosgene, triphosgene, etc.), and so on.

An amount of the halogenating agent is at least one equivalent to the benzoic acid derivative (5).

Preferably, a catalytic amount of an organic base is used in the halogenation reaction. Examples of the organic base are dimethylformamide and pyridines. Specific examples of the pyridine are pyridine, monoalkyl-substituted pyridines (e.g. picoline, ethylpyridine, propylpyridine, butylpyridine, tert.-butylpyridine, etc.), and dialkyl-substituted pyridines (e.g. 2,3-dimethylpyridine, 2,4-dimethylpyridine, 2,5-dimethylpyridine, 2,6-dimethylpyridine, 3,5-dimethylpyridine, 2-methyl-5-ethylpyridine, 2,6-diisopropylpyridine, 2,6-di-tert.-butylpyridine, etc.).

An amount of the organic base is usually from 0.005 to 0.5 equivalent, preferably 0.005 to 0.1 equivalent to the benzoic acid derivative (5).

A reaction temperature in the halogenation reaction is usually from −80° to +150° C., preferably from −30° to 100° C., while the upper limit of the reaction temperature may depend on the boiling point of the solvent.

A reaction time is not limited, and a reaction can be terminated when the benzoic acid derivative (5) disappears.

The solution of the acid halide (6) in the aromatic hydrocarbon solvent is used in the next amidation reaction step without isolating the acid halide (6) after optional removal of the excessive halogenating agent by, for example, distillation, while the acid halide (6) may be isolated and used in the amidation reaction.

Preparation of the aromatic amide compound (1)

The acid halide (6) in the aromatic hydrocarbon solvent is reacted with the aromatic amine (7) to obtain the aromatic amide compound (1).

The aromatic amine (7) may be used in the form of a free amine or an acid addition salt. Herein, the free amine and its acid addition salt are collectively referred to as "aromatic amine (7)".

Examples of the acid addition salt are inorganic acid salts such as a hydrochloride, a sulfate, a nitrate, a phosphate, a hydrobromide, a hydroiodide, etc.; and organic acid salts such as acetate, a lactate, a tartrate, a benzoate, a citrate, a methanesulfonate, an ethanesulfonate, a benzenesulfonate, a toluenesulfonate, an isethionate, a glucuronate, a gluconate, etc.

An amount of the aromatic amine (7) is usually from 0.2 to 5 moles, preferably from 0.5 to 2 moles per one mole of the acid halide (6).

The reaction of the acid halide (6) and the aromatic amine (7) can be performed by (i) adding the aromatic amine (7) or its solution in an aromatic hydrocarbon solvent to the solution of the acid halide (6) in the aromatic hydrocarbon solvent, (ii) adding the solution of the acid halide (6) in the aromatic hydrocarbon solvent to the aromatic amine (7) or its solution in an aromatic hydrocarbon solvent, or (iii) adding the solution of the acid halide (6) in the aromatic hydrocarbon solvent and the aromatic amine (7) or its solution in an aromatic hydrocarbon solvent to a reactor at the same time. Among them, the latter two methods (ii) and (iii) are preferred to suppress side reactions.

In this reaction, an acid scavenger may be used if necessary. Examples of the acid scavenger are alkali metal hydroxides (e.g. lithium hydroxide, sodium hydroxide, potassium hydroxide, etc.), alkaline earth metal hydroxides (e.g. calcium hydroxide, barium hydroxide, etc.), iron group metal hydroxides (e.g. iron hydroxide, etc.), alkali metal carbonates (e.g. lithium carbonate, sodium carbonate, potassium carbonate, etc.), alkaline earth metal carbonates (e.g. magnesium carbonate, calcium carbonate, barium carbonate, etc.), alkali metal hydrogencarbonates (e.g. sodium hydrogencarbonate, potassium hydrogencarbonate, etc.), and so on.

An amount of the acid scavenger is usually from 1 to 10 equivalents, preferably from 1 to 5 equivalents to the benzoic acid derivative (5).

When the acid scavenger is used, the reaction is performed by adding the solution of the acid halide (6) in the aromatic hydrocarbon solvent and the acid scavenger to the solution of the aromatic amine (7) in the aromatic hydrocarbon solvent. The acid scavenger may be added to the solution of the aromatic amine (7) in the aromatic hydrocarbon solvent before, during or after the addition of the solution of the acid halide (6).

Alternatively, the acid scavenger can be used in the form of an aqueous solution, as long as pH of the reaction system does not become too high. For example, the acid halide (6) and the aqueous solution of the acid scavenger are added at the same time to maintain pH of the reaction system to 7 or less, or the aqueous solution is added after the addition of the acid halide (6).

A reaction temperature in the amide-forming reaction is usually from −80° to +200° C., preferably from −30° to 100° C., more preferably from 30° to 60° C., while the upper limit of the reaction temperature may depend on the boiling point of the solvent.

A reaction time is not limited, and a reaction can be terminated when the acid halide (6) or the aromatic amine (7) disappears.

After the completion of the reaction, the aromatic amide compound (1) can be recovered in a good yield by any of conventional separation methods such as extraction, phase separation, concentration, and so on. If necessary, the recovered aromatic amide compound (1) may be purified by any of conventional purification methods such as recrystallization. Alternatively, the aromatic amide compound (1) in the aromatic hydrocarbon solvent may be used as an intermediate in the preparation of the intended medicine without isolation.

The aromatic amide compound (1) is useful as an intermediate in the preparation of the medicine, and can be prepared by the process of the present invention in a high yield in an industrial scale advantageously.

EXAMPLES

The present invention will be illustrated by the following Examples, which do not limit the scope of the present invention in any way.

Termination of the reaction in each reaction step was confirmed by the disappearance of one of the starting materials in each step which was revealed by high performance liquid chromatography (an area. percentage method).

A purity of the product in each step was measured by high performance liquid chromatography (an internal standard method). With the acid halide (6), it was converted to an derivative with aniline and analyzed by the liquid chromatography.

EXAMPLE 1

(1) In a reactor, 4-phenyl-1-bromobutane (50.0 g), methyl p-hydroxybenzoate (39.3 g), anhydrous potassium carbonate (48.7 g), sulfolane (42.2 g) and toluene (100 g) were charged, and reacted at 95° C. for 9 hours.

Thereafter, the reaction mixture was washed with water, and phase separated, followed by removal of an aqueous layer. To an organic layer, methanol (50 g) and 27% aqueous sodium hydroxide solution (82.0 g) were added and heated to react under reflux (70°–75° C.) for 2 hours.

After the completion of the reaction, sulfuric acid was added to an aqueous layer to acidify it. After removing the aqueous layer, a part of toluene was evaporated off from the organic layer to obtain a solution of 4-(4-phenyl-1-butoxy)benzoic acid in toluene (123.5 g corresponding to 62.4 g as converted to 100% purity). Yield of the pure product, 98.4%.

(2) To the solution of 4-(4-phenyl-1-butoxy)benzoic acid in toluene obtained in the above step (1) (92.8 g corresponding to 46.9 g as converted to 100% purity), dimethylformamide (0.2 g) was added, and the mixture was heated to 65° to 75° C. To the resulting solution, thionyl chloride (22.5 g) was dropwise added over a period of 15 minutes at the same temperature.

After the completion of the reaction, excessive thionyl chloride was evaporated off under reduced pressure to obtain a solution of 4-(4-phenyl-1-butoxy)benzoyl chloride in toluene (79.3 g). This solution was used in the next step without purification.

(3) In a reactor, toluene (160 g) and 3-amino-2-hydroxyacetophenone (hereinafter referred to as "AHA") sulfate (the molecular weight, 249.3. 42.3 g) were charged and heated to 40° C. At the same temperature, to this solution, the solution of 4-(4-phenyl-1-butoxy)benzoyl chloride in toluene (79.3 g) obtained in the above step (2) and an aqueous solution of sodium carbonate (1.6 equivalents to 4-(4-phenyl-1-butoxy)benzoic acid) were dropwise added simultaneously over a period of one hour, followed by heating at the same temperature for 2 hours.

After the completion of the reaction, the reaction mixture was neutralized with hydrochloric acid. An organic layer was washed with water and phase separated. Then, the organic layer was cooled to 0° C. and maintained at that temperature to crystallize the product to obtain 3-[4-(4-phenyl-1-butoxy)benzoyl]amino-2-hydroxyacetophenone (66.8 g). Yield of the pure product, 97.3% (based on AHA sulfate). Purity, 99.8%.

EXAMPLE 2

(1) In a reactor, 4-phenyl-1-bromobutane (30.1 g), methyl p-hydroxybenzoate (27.8 g), anhydrous potassium carbonate (29.1 g), dimethylsulfoxide (11.0 g) and toluene (120 g) were charged, and reacted under reflux (115°–120° C.) for 6 hours.

Thereafter, the reaction mixture was washed with water, and phase separated, followed by removal of an aqueous layer. To an organic layer, methanol (30 g) and 27% aqueous sodium hydroxide (41.8 g) were added and heated to react under reflux (70°–75° C.) for 3 hours.

After the completion of the reaction, sulfuric acid was added to an aqueous layer to acidify it. After removing the aqueous layer, a part of toluene was evaporated off from the organic layer to obtain a solution of 4-(4-phenyl-1-butoxy) benzoic acid in toluene (74.2 g corresponding to 37.1 g as converted to 100% purity). Yield of the pure product, 97.2%.

(2) To the solution of 4-(4-phenyl-1-butoxy)benzoic acid in toluene obtained in the above step (1) (46.6 g corresponding to 3.3 g as converted to 100% purity), dimethylformamide (0.1 g) was added, and the mixture was heated to 65° to 75° C. To the resulting solution, thionyl chloride (11.2 g) was dropwise added over a period of 15 minutes at the same temperature, and the mixture was maintained at the same temperature for 30 minutes.

After the completion of the reaction, excessive thionyl chloride was evaporated off under reduced pressure to obtain a solution of 4-(4-phenyl-1-butoxy)benzoyl chloride in toluene (41.1 g). This solution was used in the next step without purification.

(3) In a reactor, toluene (80 g) and AHA hydrochloride (the molecular weight, 187.6. 15.9 g) were charged and heated to 40° C. At the same temperature, to this solution, the solution of 4-(4-phenyl-1-butoxy)benzoyl chloride in toluene (41.1 g) obtained in the above step (2) and an aqueous solution of sodium carbonate (1.2 equivalents to 4-(4-phenyl-1-butoxy)benzoic acid) were dropwise added simultaneously over a period of one hour, followed by heating at the same temperature for 2 hours.

After the completion of the reaction, the reaction mixture was neutralized with hydrochloric acid. An organic layer was washed with water and phase separated. Then, the organic layer was cooled to 0° C. and maintained at that temperature to crystallize the product to obtain 3-[4-(4-phenyl-1-butoxy)benzoyl]amino-2-hydroxyacetophenone (33.4 g). Yield of the pure product, 96.9% (based on AHA hydrochloride). Purity, 99.6%.

EXAMPLE 3

(1) In a reactor, 4-phenyl-1-bromobutane (30.0 g), methyl p-hydroxybenzoate (23.7 g), anhydrous potassium carbonate (29.3 g), dimethylsulfoxide (5.5 g) and toluene (60 g) were charged, and reacted under reflux (115°–120° C.) for 6.5 hours.

Thereafter, the reaction mixture was washed with water, and phase separated, followed by removal of an aqueous layer. To an organic layer, methanol (30.6 g) and 27% aqueous sodium hydroxide (41.8 g) were added and heated to react under reflux (70°–75° C.) for one hour.

After the completion of the reaction, sulfuric acid was added to an aqueous layer to acidify it. After removing the aqueous layer, a part of toluene was evaporated off from the organic layer to obtain a solution of 4-(4-phenyl-1-butoxy) benzoic acid in toluene (73.8 g corresponding to 36.5 g as converted to 100% purity). Yield of the pure product, 95.8%.

(2) To the solution of 4-(4-phenyl-1-butoxy)benzoic acid in toluene obtained in the above step (1) (46.8 g corresponding to 23.1 g as converted to 100% purity), dimethylformamide (0.1 g) was added, and the mixture was heated to 65° to 75° C. To the resulting solution, thionyl chloride (11.0 g) was dropwise added over a period of 15 minutes at the same temperature, and the mixture was maintained at the same temperature for 30 minutes.

After the completion of the reaction, excessive thionyl chloride was evaporated off under reduced pressure to obtain a solution of 4-(4-phenyl-1-butoxy)benzoyl chloride in toluene (40.7 g). This solution was used in the next step without purification.

(3) In a reactor, toluene (80 g) and AHA sulfate (21.3 g) were charged and heated to 40° C. At the same temperature, to this solution, the solution of 4-(4-phenyl-1-butoxy) benzoyl chloride in toluene (40.7 g) obtained in the above step (2) and an aqueous solution of sodium carbonate (1.6 equivalents to 4-(4-phenyl-1-butoxy)benzoic acid) were dropwise added simultaneously over a period of one hour, followed by heating at the same temperature for 2 hours.

After the completion of the reaction, the reaction mixture was neutralized with hydrochloric acid. An organic layer was washed with water and phase separated. Then, the organic layer was cooled to 0° C. and maintained at that temperature to crystallize the product to obtain 3-[4-(4-phenyl-1-butoxy)benzoyl]amino-2-hydroxyacetophenone (33.6 g). Yield of the pure product, 95.2% (based on 4-(4-phenyl-1-butoxy)benzoic acid). Purity, 98.5%.

EXAMPLE 4

(1) In a reactor, 4-phenyl-1-bromobutane (30.0 g), methyl p-hydroxybenzoate (27.7 g), anhydrous potassium carbonate (29.3 g), N-methyl-2-pyrrolidone (14 g) and toluene (120 g) were charged, and reacted under reflux (115°–120° C.) for 10 hours.

Thereafter, the reaction mixture was washed with water, and phase separated, followed by removal of an aqueous layer. To an organic layer, methanol (30 g) and 27% aqueous sodium hydroxide (41.9 g) were added and heated to react under reflux (70°–75° C.) for 3 hours.

After the completion of the reaction, sulfuric acid was added to an aqueous layer to acidify it. After removing the aqueous layer, a part of toluene was evaporated off from the organic layer to obtain a solution of 4-(4-phenyl-1-butoxy) benzoic acid in toluene (76.0 g corresponding to 37.6 g as converted to 100% purity). Yield of the pure product, 98.9%.

(2) To the solution of 4-(4-phenyl-1-butoxy)benzoic acid in toluene obtained in the above step (1) (46.6 g corresponding to 23.1 g as converted to 100% purity), dimethylformamide (0.1 g) was added, and the mixture was heated to 65° to 75° C. To the resulting solution, thionyl chloride (11.3 g) was dropwise added over a period of 15 minutes at the same temperature, and the mixture was maintained at the same temperature for 30 minutes.

After the completion of the reaction, excessive thionyl chloride was evaporated off under reduced pressure to obtain a solution of 4-(4-phenyl-1-butoxy)benzoyl chloride in toluene (41.1 g). This solution was used in the next step without purification.

(3) In a reactor, toluene (80 g) and AHA hydrochloride (16.0 g) were charged and heated to 40° C. At the same temperature, to this solution, the solution of 4-(4-phenyl-1-butoxy)benzoyl chloride in toluene (41.4 g) obtained in the above step (2) and an aqueous solution of sodium carbonate (1.3 equivalents to 4-(4-phenyl-1-butoxy)benzoic acid) were dropwise added simultaneously over a period of one hour, followed by heating at the same temperature for 2 hours.

After the completion of the reaction, the reaction mixture was neutralized with hydrochloric acid. An organic layer was washed with water and phase separated. Then, the organic layer was cooled to 0° C. and maintained at that temperature to crystallize the product to obtain 3-[4-(4-phenyl-1-butoxy)benzoyl]amino-2-hydroxyacetophenone (32.1 g). Yield of the pure product, 93.3% (based on AHA hydrochloride). Purity, 99.1%.

EXAMPLE 5

(1) In a reactor, 4-phenyl-1-bromobutane (38.2 g), methyl p-hydroxybenzoate (29.9 g), anhydrous potassium carbonate (37.1 g), sulfolane (12.9 g) and toluene (76.2 g) were charged, and reacted under reflux (115°–120° C.) for 8 hours.

Thereafter, the reaction mixture was washed with water, and phase separated, followed by removal of an aqueous layer. To an organic layer, methanol (19.1 g) and 27% aqueous sodium hydroxide (39.6 g) were added and heated to react under reflux (70°–75° C.) for 1.5 hours.

After the completion of the reaction, sulfuric acid was added to an aqueous layer to acidify it. After removing the aqueous layer, a part of toluene was evaporated off from the organic layer to obtain a solution of 4-(4-phenyl-1-butoxy) benzoic acid in toluene (216.0 g corresponding to 47.3 g as converted to 100% purity). Yield of the pure product, 97.6%.

(2) To the solution of 4-(4-phenyl-1-butoxy)benzoic acid in toluene obtained in the above step (1) (216.0 g corresponding to 47.3 g as converted to 100% purity), dimethylformamide (0.2 g) was added, and the mixture was heated to 65° to 75° C. To the resulting solution, thionyl chloride (22.4 g) was dropwise added over a period of 15 minutes at the same temperature, and the mixture was maintained at the same temperature for one hour.

After the completion of the reaction, excessive thionyl chloride was evaporated off under reduced pressure to obtain a solution of 4-(4-phenyl-1-butoxy)benzoyl chloride in toluene (146.5 g). This solution was used in the next step without purification.

(3) In a reactor, toluene (162.0 g) and AHA sulfate (43.3 g) were charged and heated to 45° C. At the same temperature, to this solution, the solution of 4-(4-phenyl-1-butoxy)benzoyl chloride in toluene (146.5 g) obtained in the above step (2) and an aqueous solution of sodium carbonate (1.6 equivalents to 4-(4-phenyl-1-butoxy)benzoic acid) were dropwise added simultaneously over a period of one hour, followed by heating at the same temperature for 2 hours.

After the completion of the reaction, the reaction mixture was neutralized with hydrochloric acid. An organic layer was washed with water and separated. Then, the organic layer was cooled to 0° C. and maintained at that temperature to crystallize the product to obtain 3-[4-(4-phenyl-1-butoxy)benzoyl]amino-2-hydroxyacetophenone (68.8 g). Yield of the pure product, 96.7% (from the step (2), based on 4-(4-phenyl-1-butoxy)benzoic acid). Purity, 99.6%.

What is claimed is:

1. A process for preparing a compound of the formula (1):

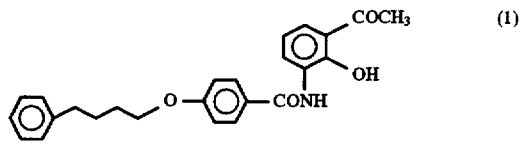

comprising the steps of:

reacting a benzoate of the formula (2):

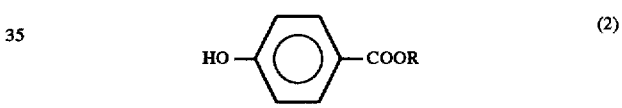

wherein R is a straight or branched lower alkyl group and a haloalkylbenzene of the formula (3):

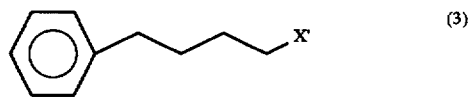

wherein $X^1$ is a halogen atom in the presence of a basic compound and an aprotic polar compound in an aromatic hydrocarbon solvent to obtain an ether of the formula (4):

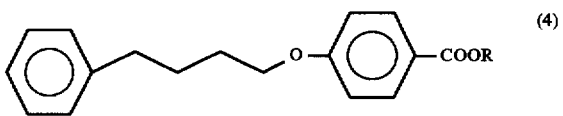

wherein R is the same as defined above, alkali hydrolyzing said ether (4) in an aromatic hydrocarbon solvent and precipitating a hydrolysate with an acid to obtain a benzoic acid derivative of the formula (5):

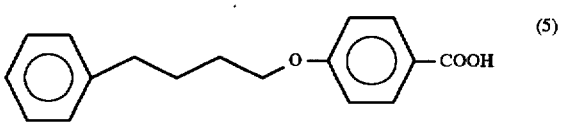

reacting said benzoic acid derivative (5) in an aromatic hydrocarbon solvent with a halogenating agent to obtain an acid halide of the formula (6):

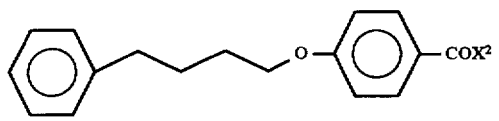

wherein $X^2$ is a halogen atom, and reacting said acid halide (6) in an aromatic hydrocarbon solvent with an aromatic amine of the formula (7):

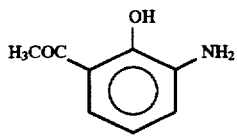

2. The process according to claim 1, wherein said aprotic polar compound is at least one compound selected from the group consisting of dimethylsulfoxide, sulfolane and N-methyl-2-pyrrolidone.

3. The process according to claim 1, wherein said acid halide (6) and said aromatic amine (7) are reacted at a temperature in the range between 30° C. and 60° C.

4. The process according to claim 1, wherein said ether (4) in the aromatic hydrocarbon solvent is hydrolyzed after washing with water.

5. The process according to claim 1, wherein said hydrolysis is performed in the presence of an alcohol.

6. The process according to claim 1, wherein the same kind of the aromatic hydrocarbon solvent is used in all steps.

7. A process for preparing an ether of the formula (4):

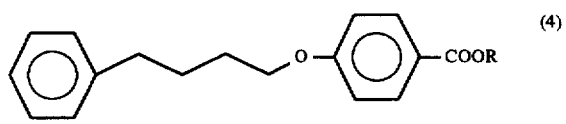

wherein R is a straight or branched lower alkyl group, comprising reacting a benzoate of the formula (2):

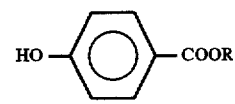

R is the same as defined above, and a haloalkylbenzene of the formula (3):

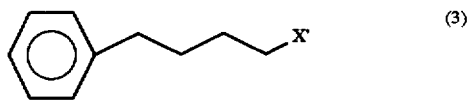

wherein $X^1$ is a halogen atom in the presence of a basic compound and an aprotic polar compound in an aromatic hydrocarbon solvent.

8. The process according to claim 7, wherein said aprotic polar compound is at least one compound selected from the group consisting of dimethylsulfoxide, sulfolane and N-methyl-2-pyrrolidone.

* * * * *